United States Patent [19]

Barbier et al.

[11] Patent Number: 4,983,746

[45] Date of Patent: Jan. 8, 1991

[54] OXETANONES AND PROCESS FOR THEIR PRODUCTION

[75] Inventors: Pierre Barbier, Rixheim, France; Fernand Schneider, Basel; Ulrich Widmer, Rheinfelden, both of Switzerland

[73] Assignee: Hoffmann-La Roche Inc., Nutley, N.J.

[21] Appl. No.: 391,732

[22] Filed: Aug. 8, 1989

Related U.S. Application Data

[63] Continuation of Ser. No. 195,335, May 18, 1988, abandoned, which is a continuation of Ser. No. 801,345, Nov. 25, 1985, abandoned.

[30] Foreign Application Priority Data

Dec. 21, 1984 [CH] Switzerland ............... 6101/84
Sep. 19, 1985 [CH] Switzerland ............... 4067/85

[51] Int. Cl.$^5$ ............................................. C07D 305/12
[52] U.S. Cl. ............................................. 549/328
[58] Field of Search ............................................. 549/328

[56] References Cited

FOREIGN PATENT DOCUMENTS 0185359 6/1986 European Pat. Off. ............ 549/328
0189577 8/1986 European Pat. Off. ............ 549/328

OTHER PUBLICATIONS

Mitsunobo, Oyo, Synthesis, No. 1, (Jan. 1981), pp. 1–3.

*Primary Examiner*—Glennon H. Hollrah
*Assistant Examiner*—Amelia A. Owens
*Attorney, Agent, or Firm*—George M. Gould; William H. Epstein; Dennis P. Tramaloni

[57] ABSTRACT

The invention is directed to a process for the manufacture of pancreatic lipase-inhibiting oxetanone ethyl esters of the formula

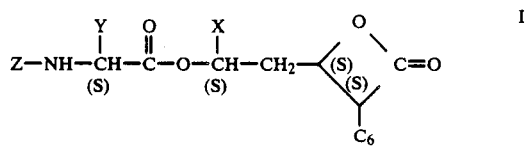

wherein X is undecyl or 2Z,5Z-undecadienyl; $C_6$ is n-hexyl; Y is isobutyl and Z is formyl or Y is carbamoylmethyl and Z is acetyl;

which process comprises esterifying the corresponding oxetanone ethanols, or hydrogenating the 3-undecenyl group in corresponding oxetanone ethyl ester starting materials to the undecyl group X, or N-formylating or N-acetylating corresponding primary amines.

5 Claims, No Drawings

OXETANONES AND PROCESS FOR THEIR PRODUCTION

This application is a continuation of 07/195,335 filed May 18, 1988 which is a continuation of 06/801,345 Nov. 25, 1985 both now abandoned.

SUMMARY OF THE INVENTION

The present invention is directed to a novel process for the manufacture of oxetanones of the formula

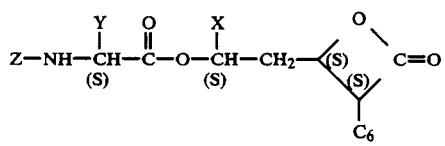

wherein X is undecyl or 2Z,5Z-undecadienyl, $C_6$ is n-hexyl, Y is isobutyl and Z is formyl or Y is carbamoylmethyl and Z is acetyl.

The compounds of formula I in which Y is isobutyl and Z is formyl are novel. They have valuable pharmacological properties. In particular, they inhibit pancreatic lipase and can accordingly be used for the control or prevention of illnesses, especially of obesity, hyperlipaemia, atherosclerosis and arteriosclerosis.

DETAILED DESCRIPTION OF THE INVENTION

The invention is directed to a process for the production of oxetanone derivatives of the formula

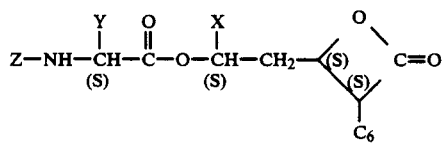

wherein X is undecyl or 2Z,5Z-undecadienyl; $C_6$ is n-hexyl; Y is isobutyl and Z is formyl or Y is carbamoylmethyl and Z is acetyl;
which process comprises esterifying an acid of the formula

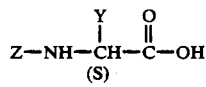

wherein Z and Y are as defined in Formula I:
with an alcohol of the formula

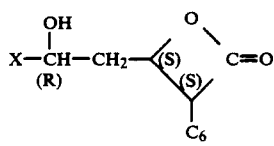

wherein X and $C_6$, are as defined in Formula I.
Alternatively, the compounds of Formula I may be prepared by hydrogenating an oxetanone of the formula

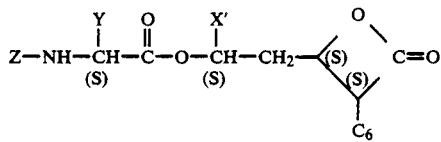

wherein X' is 3-undecenyl and $C_6$, Y and Z are as defined in Formula I.
or by treating an oxetanone of the formula

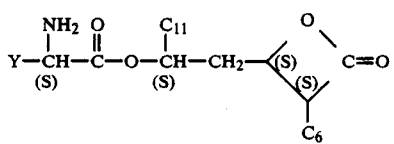

wherein $C_{11}$ is undecyl and Y and $C_6$ are as defined in Formula I;
with an alkanoylating agent which introduces the group Z, wherein Z is as defined in Formula I.

The esterification of the acid of Formula II with an alcohol of Formula III, can be carried out in a solvent, e.g., an ether such as tetrahydrofuran (THF), and in the presence of triphenylphosphine and diethyl azodicarboxylate. The temperature is not critical; the esterification is preferably carried out at room temperature.

The hydrogenation of the oxetanones of Formula I' can be carried out in a solvent, e.g., an ether such as THF, in the presence of a hydrogenation catalyst such as palladium-on-carbon, preferably at about room temperature.

As used herein, the term "alkanoylating agent" refers to an acid anhydride, specifically formic acid anhydride or acetic acid anhydride or a mixed acid anhydride such as formic acid/acetic acid anhyyride. The alkanoylation is preferably carried out in a solvent, e.g., an ether such as THF and preferably at room temperature.

The alcohols of Formula III can be prepared by cleaving off the ether group L in an ether of the formula

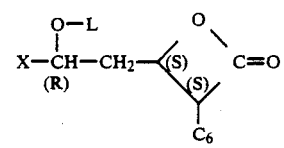

wherein $C_6$ and X are as defined fined in Formula I and L is a readily cleavable ether group such as tetrahydro-2H-pyran-2-yl. 1-ethoxyethyl or t-butyldimethylsilyl.

This cleavage can be carried out in a solvent, e.g., an alcohol such as ethanol, in the presence of an acid catalyst such as pyridinium-4-toluenesulphonate while heating, e.g., to 50°–65° C.

The ethers of Formula IV can be prepared by cyclizing a compound of the formula

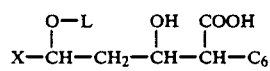

This cyclization reaction can be carried out in the presence of benzenesulphonyl chloride in a solvent such as pyridine while cooling, e.g., to 0° C.

The acids of Formula V can be prepared either by saponifying a corresponding ester of the formula $$\underset{(R)}{\text{X}-\underset{|}{\overset{\text{O}-\text{L}}{\text{CH}}}-\text{CH}_2-\underset{|}{\overset{\text{OH}}{\text{CH}}}-\underset{|}{\overset{\text{COOR}}{\text{CH}}}-\text{C}_6} \quad \text{VI}$$

wherein R is straight-chain or branched $C_{1-4}$-alkyl such as methyl, ethyl or t-butyl and L, X and $C_6$ are as defined in Formula IV.

Alternatively, where X is a 2Z,5Z-undecadienyl residue, by condensing octanoic acid with an aldehyde of the formula $$\underset{(R)}{\text{X}-\underset{|}{\overset{\text{O}-\text{L}}{\text{CH}}}-\text{CH}_2-\text{CHO}} \quad \text{VII}$$

wherein X and L are as defined in Formula VI.

The saponification of the ester VI can be carried out with an alcoholic alkali metal hydroxide solution such as a methanolic potassium hydroxide solution by beating at a temperature up to the reflux temperature of the reaction mixture.

The condensation of an aldehyde VII with octanoic acid can be carried out in a solvent such as THF in the presence of diisopropylamine and butyl lithium while cooling, e.g., to −50° C.

The acids of Formula V, which are present in the (5R)-or (5S)-form, can be converted in the following manner into the (2S,3S,5R)- or (2R,3R,5S)-steroisomers:

A (5R)- or (5S)-acid of Formula V is cyclized, e.g., by means of toluene-4-sulphonic acid monohydrate while heating to 50°-60° C. in ethanol, to the corresponding (6R)- or (6S)-pyrandione of the formula

V-A wherein L' stands for hydrogen and X and $C_6$ are as defined in Formula IV.

This (6R)- or (6S)-pyrandione is then oxidized, e.g., in acetone by means of Jones' reagent at a temperature below 25° C., to the corresponding pyrandione and the latter is stereo specifically hydrogenated, e.g., in ethyl acetate in the presence of platinum oxide, to the (3S,4S,6R)- or (3R 4R,6S)-pyrandione of Formula V-A in which L' is hydrogen. This pyrandione is converted into a compound of Formula V-A in which L' stands for an ether protecting group such as t-butyldimethylsilyl, e.g., by means of t-butyldimethylchlorosilane in dimethylformamide. The cyclic (3S,4S,6R)- or (3R,4R,6S)-ether obtained is cleaved, e.g., by reaction with an aqueous potassium hydroxide solution in dioxan, and the resulting compound is converted in situ into a (2S,3S,5R)- or (2R,3R,5S)-ether of the formula $$\text{X}-\underset{|}{\overset{\text{OL''}}{\text{CH}}}-\text{CH}_2-\underset{|}{\overset{\text{OL'}}{\text{CH}}}-\underset{|}{\overset{\text{COOR'}}{\text{CH}}}-\text{C}_6 \quad \text{V-B}$$

wherein L" stands for hydrogen, L' is the same ether protecting group as in the ether V-A, R' is benzyl or p-nitrobenzyl and X and $C_6$ are as defined in Formula IV. The ether V-B obtained is then converted into a diethyl of the same formula in which L'" stands for an ether protecting group such as tetrahydro-2H-pyran-2-yl. After cleaving off firstly the ether protecting group L', e.g., with tetrabutylammonium fluoride trihydrate in THF, and then the group R', e.g by hydrogenation in THF in the presence of Pd/C, there is obtained the desired (2S,3S,5R)- or (2R,3R,5S)-acid of Formula V.

The esters VI can be prepared either by n-hexylating a corresponding ester of the formula $$\underset{(R)}{\text{X}-\underset{|}{\overset{\text{O}-\text{L}}{\text{CH}}}-\text{CH}_2-\underset{|}{\overset{\text{OH}}{\text{CH}}}-\text{CH}_2-\text{COOR}} \quad \text{VIII}$$

(wherein X, L and R are as defined in Formula VI), or by reducing a β-ketoester of the formula $$\text{X}-\underset{|}{\overset{\text{OL}}{\text{CH}}}-\text{CH}_2-\underset{\|}{\overset{\text{O}}{\text{C}}}-\underset{|}{\overset{\text{COOR}}{\text{CH}}}-\text{C}_6 \quad \text{IX}$$

(wherein X, L, R and $C_6$ are as defined in Formula VI).

The n-hexylation of an ester VIII can be carried out by reacting the ester IX in a solvent such as THF with a solution of n-butyl lithium in n-hexane in the presence of diisopropylamine at about −50° C. and subsequently reacting with a solution of a hexyl halide such as 1-bromohexane in hexamethylphosphoric acid triamide at a temperature of about 0° to 10° C.

The reduction of a β-ketoester IX can be carried out, if desired in an inert gas such as argon in a solvent such as an ether, e.g. THF, with a complex metal hydride such as sodium borohydride (NaBH$_4$) at a temperature below about 0° C.

The esters VIII can be prepared by the reductive cleavage of a sulphoxide of the formula $$\underset{(R)}{\text{X}-\underset{|}{\overset{\text{O}-\text{L}}{\text{CH}}}-\text{CH}_2-\underset{(S)}{\underset{|}{\overset{\text{OH}}{\text{CH}}}}-\underset{|}{\overset{\text{COOR}}{\text{CH}}}-\text{S}\underset{\searrow T}{\overset{\nearrow \text{O}}{}}} \quad \text{X}$$

wherein T is p-tolyl and L, R and X are as defined in Formula VI.

This reduction can be carried out by means of aluminum amalgam in a solvent such as THF and water.

The β-ketoesters IX can be obtained by reacting an aldehyde of the Formula X-CHO; with a $C_{1-4}$-alkyl 2-acetyloctanoate and esterifying the resulting alcohol of the formula $$\text{X}-\underset{|}{\overset{\text{OH}}{\text{CH}}}-\text{CH}_2-\underset{\|}{\overset{\text{O}}{\text{C}}}-\underset{|}{\overset{\text{COOR}}{\text{CH}}}-\text{C}_6 \quad \text{XI}$$

(wherein X, R and $C_6$ are as defined in Formula VI).

The conversion of an aldehyde X-CHO into an alcohol XI can be carried out as described in Example 1L.

The sulphoxides X can be prepared by condensing an aldehyde of Formula VII with an ester of the formula $$\underset{T}{\overset{O}{\nwarrow}}S-CH_2-COOR \qquad \text{XII}$$

e.g., as described in Example (1H).

The aldehydes of Formula VII can be prepared by reducing a corresponding ester of the formula $$X-\underset{(R)}{\overset{O-L}{CH}}-CH_2-COOR \qquad \text{XIII}$$

wherein X, L and R are as defined in Formula VII. e.g., with diisobutylaluminum hydride in a solvent such as toluene at a temperature of about −60° to 80° C.

The esters of Formula XIII can be prepared starting from the aldehydes of the Formula X-CHO via the sulphoxides of the formula $$X-\underset{(R)}{\overset{OH}{CH}}-\overset{COOR}{CH}-S\overset{\nearrow O}{\searrow T} \qquad \text{XIV}$$

and the alcohols of the formula $$X-\underset{(R)}{\overset{OH}{CH}}-CH_2-COOR \qquad \text{XV}$$

e.g., as described in Examples (1H.b), (1I.b) and (1K.a).

The oxetanone starting materials of Formula I' can be prepared in an analogous manner to the oxetanones of Formula I starting from esters of Formula XIII in which a 3-undecenyl residue X' is present in place of the group X via the corresponding compounds of Formulae III-XI.

The oxetanone starting materials of Formula I'' can be prepared by cleaving off the amino protecting group W in an oxetanone of the formula $$W-NH-\underset{(S)}{\overset{Y}{CH}}-\overset{O}{\overset{\|}{C}}-O-\underset{(S)}{\overset{X}{CH}}-CH_2-\underset{C_6}{\overset{(S)}{\diamondsuit}}C=O \qquad \text{I'''}$$

wherein X is undecyl and Y and $C_6$ are as defined in Formula I. Benzyloxycarbonyl and p-nitrobenzyloxycarbonyl can be mentioned as examples of an amino protecting group W. The cleavage of W can be carried out by hydrogenation in a solvent, e.g., an ether such as THF, in the presence of a hydrogenation catalyst such as palladium-on-carbon, preferably at room temperature. An undecadienyl group X present in I''' is hydrogenated to the undecyl group during the hydrogenolytic cleavage of W.

The oxetanones of Formula I''' can be prepared by sterifying an alcohol of the formula $$X-\underset{(S)}{\overset{OH}{CH}}-CH_2-\underset{C_6}{\overset{(S)}{\diamondsuit}}C=O \qquad \text{III'}$$

with an acid anhydride obtained by reacting an acid of the formula $$Y-\underset{(S)}{\overset{NH_2}{CH}}-\overset{O}{\overset{\|}{C}}-O-\underset{(S)}{\overset{C_{11}}{CH}}-CH_2-\underset{C_6}{\overset{(S)}{\diamondsuit}}C=O \qquad \text{I''}$$

with dicyclohexylcarbodiimide or N-ethyl-N'-(3-dimethylaminopropyl)-carbodiimide hydrochloride. The preparation of this acid anhydride can be carried out in a solvent such as methylene chloride while cooling, e.g. to 2°-3° C., and the subsequent esterification can be carried out in a solvent such as dimethylformamide.

The alcohols of Formula III' are the (S)-epimers of the alcohols of Formula III and can be prepared in a similar manner starting from the aldehydes of the Formula X-CHO via the (S)-enantiomers of the esters of Formula XV, via the (S)-enantiomers of the ethers of Formulae XIII and VII, and via the (S)-epimers of the compounds of Formulae VIII, VI, V and IV.

(R)-α-(Hydroxydiphenylmethyl)benzyl acetate can be used in place of a sulphinyl ester XII for the conversion of an aldehyde of the Formula X-CHO or of the (S)-enantiomer of an aldehyde of Formula VII into the corresponding (S)-enantiomer of an ester of Formula XV or VIII, respectively. In this case there is obtained as an intermediate in place of a sulphoxide of Formula XIV or X the (R)-2-hydroxy-1,2,2,-triphenylethyl ester corresponding to the alkyl esters of Formulae XV or VIII.

The esters of the formula $$X'-\underset{(R)}{\overset{O-L}{CH}}-CH_2-COOR \qquad \text{XIII-A}$$

can be prepared in the same manner as the esters XIII or starting from a heptenoic acid ester of the formula $$\underset{}{\overset{CH_2}{\|}}\underset{}{\overset{}{CH}}-CH_2-\underset{(R)}{\overset{O-L}{CH}}-CH_2-COOR \qquad \text{XVI}$$

via an aldehyde of the formula $$\overset{O}{\overset{\|}{CH}}-CH_2-\underset{(R)}{\overset{O-L}{CH}}-CH_2-COOR \qquad \text{XVII}$$

e.g., as described in Example 1M.

EXAMPLE 1

1A. Manufacture of an oxetanone of Formula I (1A.a) To a solution of 100 mg of rac-3-hexyl-4-(2-hydroxy-tridecyl)-2-oxetanone(2R,3S,4S:2S,3R,4R) or of 100 mg of (3S,4S)-3-hexyl-4-[(R)-2-hydroxytridecyl]-2-oxetanone, 74 mg of triphenylphosphine and 45 mg of N-formyl-L-leucine in 2 ml of THF are added dropwise while stirring 44.3 µl of diethyl azodicarboxylate. After stirring overnight the organic phase is evaporated in vacuo and the residue is purified by chromatography on silica gel with toluene-ethyl acetate (9:1). There are obtained 20 or 37 mg of N-formyl-L-leucine (S)-1-[[(2S,3S)-3-hexyl-4-oxo-2-oxetanyl]methyl]dodecyl ester, $[\alpha]_D^{20} = -33°$ C. (c=0.36, CHCL$_3$).

(1A.b) A solution of 2.5 mg of N-formyl-L-leucine (S,4Z)-1-[[(2S.3S)-3-hexyl-4-oxo-2-oxetanyl]methyl]-4-dodecenyl ester in 0.1 ml of THF is treated with 1 mg of palladium-on-carbon, then hydrogenated for 3 hours. The catalyst is filtered off and the filtrate is chromatographed over silica gel with toluene/ethyl acetate (9:1), -[[(2S,3S)-3-hexyl-4-oxo-2-oxetanyl]methyl]-4-dodecyl ester, +H-NMR spectrum (270 MHz, CDCl$_3$): 0.89 (6H); 0.97 (6H); 1.15–2.25 (34H); 3.22 (2H); 4.29 (1H) 4.70 (1H); 5.04 (1H); 5.91 (1H); 8.23 (1H) ppm.

(1A.c) Analogously to (a) there are obtained:
(1) N-acetyl-3-carbamoyl-L-alanine (S)-1-]][(2S,3S)-3-hexyl-4-oxo-2-oxetanyl]methyl]dodecyl ester, MS: M$_+$(510); (M+1)$^+$(511);
(2) N-formyl-L-leucine (S)-1-[[(2S,3S)-3-hexyl-4-oxo-2-oxetanyl]methyl]-3Z,6Z-dodecadienyl ester, $[\alpha]_D^{20} = -33°$ C. (c=0.36, CHCL$_3$); MS: (M+1)$^+$ (492);
(3) N-formyl-L-leucine (S,4Z)-1-[[(2S,3S)-3-hexyl-4-oxo-2-oxetanyl]methyl]-4-dodecenyl ester.

1B. Preparation of the alcohol starting materials of Formula III (1B.a) 265 mg of an isomer mixture of 3-hexyl-4-[2-[(tetrahydro-2H-pyran-2-yl)oxy]tridecyl]-2-oxetanone are dissolved in 2.5 ml of ethanol and 13 mg of pyridinium-4-toluenesulphonate are added. The reaction mixture is heated to 55°–60° C. until the reaction has finished. The solvent is removed in vacuo and the residue is taken up in ether, whereby there separate crystals which are removed by filtration. The solvent is evaporated off in vacuo and the residue is chromatographed on silica gel. There is obtained rac-3-hexyl-4-(2-hydroxytridecyl-2-oxetanone (2R,3S,4S:2S, 3R,4R), MS: M$^+$ (354), m.p. 44.5°–46° C.

In an analogous manner there are obtained:
(1B.b) (3S,4S)-3-Hexyl-4-[(R)-2-hydroxytridecyl]-2-oxetanone, m.p. 46°–46.5° C.;
(1B.c) (3S,4S)-3-hexyl-4-[(R)-2-hydroxy-4Z.7Z-tridecadienyl-2-oxetanone;
(1B.d) trans-3-hexyl-4-[(R)-2-hydroxy-5Z-tridecenyl]-2-oxetanone.

1C. Preparation of the ethers of Formula IV (1C.a) 0.7 g of an isomer mixture of 2-hexyl-3-hydroxy-5-[(tetrahydro-2H-pyran-2-yl)oxy]hexadecanoic acid is dissolved in 15 ml of pyridine and cooled to 0° C. After the dropwise addition of 0.4 ml of benzenesulphonyl chloride the mixture is stirred at 0° C. The reaction mixture is poured into 120 ml of 10% sodium chloride solution and extracted three times with 30 ml of diethyl ether. The combined extracts are dried filtered and evaporated. After chromatography on silica gel there is obtained an isomer mixture of 3-hexyl-4-[2-[(tetrahydro-2H-pyran-2-yl)oxy]tridecyl]-2-oxetanone; MS: (M+1)$^+$ (440).

In an analogous manner there are obtained:
(1C.b) 3-Hexyl-4-[(R)-2-[(tetrahydro-2H-pyran-2-yl)oxy]-tridecyl]-2-oxetanone;
(1C.c) 3-hexyl-4-[(R)-2-[(tetrahydro-2H-pyran-2-yl)oxy]-4Z,7Z-tridecadienyl]-2-oxetanone;
(1C.d) 3-hexyl-4-[(R)-2-[(tetrahydro-2H-pyran-2-yl)oxy]-5Z-tridecenyl]-2-oxetanone.

1D. Preparation of the acids of Formula V (1D.a) 1 g of a diastereomer mixture of t-butyl 2-hexyl-3-hydroxy(R)-5-[(tetrahydro-2H-pyran -2-yl)oxy]-hexadecanoate is heated under reflux in 17 ml of 2N methanolic potassium hydroxide solution. The reaction mixture is cooled and poured on to 60 ml of ice-water. The mixture is adjusted to a pH of 1 by the dropwise addition of 1N aqueous hydrochloric acid then extracted with ether. The combined ether phases are dried. filtered and evaporated. The oil is chromatographed on silica gel. There is obtained a diastereomer mixture of 2-hexyl-3-hydroxy(R)-5-[(tetrahydro-2H-Pyran -2-yl)oxy]hexadecancio acid.

In an analogous manner there are obtained:
(1D.b) 2-Hexyl-3-hydroxy-5-[(tetrahydro-2H-pyran-2-yl)-oxy]hexadecanoic acid
(1D.c) 2-hexyl-3-hydroxy(R)-5-[(tetrahydro-2H-pyran-2-yl)-oxy]-7Z,10Z-hexadecadenoic acid.

1E. Preparation of the acids of Formula V (Variant)

(1E.a) 2 ml of diisopropylamine in 30 ml of dry THF are cooled to −20° C. 9.68 ml of butyl lithium (1.6M/hexane) are then added dropwise in such a manner that the temperature does not exceed −20° C. The mixture is subsequently stirred for 15 minutes and then cooled to −50° C. Thereafter, 1.11 ml of octanoic acid in 10 ml of THF are added dropwise and the mixture is stirred at −=° C. for a further 10 minutes. The mixture is stirred at room temperature for 1 hour and subsequently again cooled to −50° C. 2 g of (R)-3-[(tetrahydro-2H-pyran-2.yl)oxy]5Z, 8Z-tetradecadienal in 10 ml of THF are now added dropwise. The mixture is stirred at −50° C. for 30 minutes then at room temperature for 72 hours. After hydrolysis with 2N hydrochloric acid the reaction mixture is evaporated. The residue is extracted with ether. The organic phase is dried filtered and evaporated. The material obtained is filtered through silica gel. There is obtained 2-hexyl-3-hydroxy(R)-5-[(tetrahydro-2H-pyran-2-yl)oxy]-7Z,10Z-hexadecadienoic acid.

(1E.b) In an analogous manner there is obtained:
2-Hexyl-3-hydroxy(R)-5-[(tetrahydro-2H-pyran-2-yl)-oxy]8Z-hexadecenylcarboxylic acid.

1F. Preparation of the esters of Formula VI (1F.a) 1.8 ml of diisopropylamine are cooled to −5° C. under argon and 8.7 ml of a 1.6N n-butyl lithium solution in n-hexane are added dropWise. Thereafter, the mixture is stirred for 10 minutes. After cooling to −50° C. the cooling bath is removed. A solution of 2.67 g of a diastereomer mixture of t-butyl 3-hydroxy(R)-5-[(tetrahydro-2H-pyran-2-yl)oxy]hexadecanoate in 9 ml of THF is added dropwise thereto. In so doing the temperature rises to −20° C. The mixture is left to warm to 0° C. and stirred for 10 minutes. A solution of 0.93 ml of 1-bromohexane in 4.4 ml of hexamethylphosphoric acid triamide is then added. The temperature rises to 9° C. Thereafter the mixture is left to warm to room temperature and stirred for 2½ hours. The solution is poured on to 200 ml of ice-water and saturated with sodium chloride. The mixture is extracted with ether. The combined extracts are dried filtered and evaporated. The residual oil is chromatographed on silica gel. There is obtained t-butyl 2-hexyl-3-hydroxy-(R)-5-[(tetrahydro-2H-pyran-2-yl)-oxy]hexadecanoate MS: (M-O-t-butyl)+ (439).

(1F.b) In an analogous manner there is obtained:
t-Butyl 2-hexyl-3-hydroxy(R)-5-[(tetrahydro -2H-pyran-2-yl)oxy]-7Z,10Z-hexadecadienoate.

1G. Preparation of the esters of Formula VI (variant)

7.76 g of methyl 2-hexyl-3-oxo -5-[(tetrahydro-2H-pyran-2-yl)oxy]hexadecanoate are dissolved in 500 ml of THF while gassing with argon, treated with 20 ml of ethanol and cooled to −5° C. 5.3 g of NaBH$_4$ are added portionwise while stirring in such a manner that the temperature does not exceed 0° C. After stirring for 3 hours the excess sodium borohydride is filtered off, the reaction mixture is hydrolyzed (to pH 6) with 2N hydrochloric acid in the cold and the solvent is evaporated off. The residue is extracted with ether and the ethereal phase is dried and evaporated. There are obtained 7.71 g of methyl 2-hexyl-3-hydroxy-5-[(tetrahydro-2H-pyran-2-yl)oxy]hexadecanoate.

1H. Preparation of the esters of Formulae VIII and XV 13.6 g of a diastereomer mixture of t-butyl 3-hydroxy(R)-5-tetrahydro -2H-pyran-2-yl)oxy]-2-[(S)-p-tolylsulphinyl] hexadecanoate are dissolved in a mixture of 6 l of THF and 0.6 l of water. 150 g of amalgamated aluminum foil are then added portionwise within 6 hours. In so doing the temperature is held between 15° C. and 20° C. After completion of the addition the mixture is stirred until the reaction has finished. The insoluble material is filtered off under suction and washed firstly with 1 l of THF, then with 2 ml of THF. The filter cake is taken up in 2 l of diethyl ether, stirred well and again filtered under suction. This procedure is repeated once. The combined organic phases are evaporated and the oily residue is purified by chromatography or silica gel. There is obtained t-butyl 3-hydroxy(R)-5-[(tetrahydro-2H-pyran-2-yl)oxy]hexadecanoate, MS: (M-O-t-butyl)+ (355).

In an analogous manner there are obtained:
(1H.a) t-Butyl 3-hydroxy(R)-5-[(tetrahydro-2H-pyran -2-yl)oxy]7Z,10Z-hexadecadienoate;
(1H.b) t-butyl (R)-3-hydroxy-5Z,8Z-tetradecadienoate,- [α]$_D^{20}$=−12.67° (c=15, CHCl$_3$).

1I. Preparation of the sulphoxides of Formulae X and XIV 16.5 g of t-butyl [(S)-p-tolylsulphinyl]acetate are dissolved in a mixture of 60 ml of ether and 600 ml of THF and cooled to −78° C. 43 ml of t-butylmagnesium bromide (2N solution in ether) are then added dropwise within 30 minutes in such a manner that the temperature does not exceed −70° C. After stirring at −78° C. for 1 hour 13.4 g of (R)-3-[(tetrahydro-2H-pyran-2-yl)oxy]-tetradecanal in 100 ml of THF are added dropwise and the mixture is stirred at −78° C. for a further 2 hours. The reaction mixture is hydrolyzed with 2N hydrochloric acid and the solvent is evaporated off. The reaction mixture remaining behind is extracted with ether and the 8thereal phase is dried and evaporated. The crude product is eluted through a column of silica gel. There are obtained 14.9 g of t-butyl 3-hydroxy(R)-5-[(tetrahydro-2H-pyran-2-yl)oxy]-2-[(S)-p-tolylsulphinyl]hexadecanoate, m.p. 97°–98° C.

In an analogous manner there are obtained:
(1I.a) t-butyl 3-hydroxy(R)-5-[(tetrahydro -2H-pyran-2-yl)oxy]-2-[(S)-p-tolylsulphinyl]]7Z,10Z-hexadecadienoate;
(1I.b) t-butyl (R)-3-hydroxy-2-[(R) -p-tolylsulphinyl]-5Z,7Z-tetradecadienoate.

1J. Preparation of the aldehydes of Formula VII (1J.a) 9.2 g of t-butyl (R)-3-[(tetrahydro-2H-pyran-2-yl)oxy]tetradecanoate are dissolved in 115 ml of toluene while gassing with argon and with the exclusion of moisture and cooled to −75° C. 26.5 ml of a 1.2M DIBAH solution in toluene are then added dropwise within ¼ hour in such as manner that the temperature does not exceed −70° C. The mixture is stirred at −75° C. for a further one hour. There are then added dropwise 7.4 ml of saturated ammonium chloride solution and subsequently 15.5 ml of 1N hydrochloric acid at −70° C. The cooling bath is removed and the mixture is left to warm to room temperature. After stirring at room temperature for one hour the organic phase is separated and washed with water. The organic phase is dried, filtered and evaporated. The material obtained is chromatographed on silica gel. There is obtained [(R)-3-[(tetrahydro-2H-pyran-2-yl)oxyl]tetradecanal as a colourless oil.

In an analogous manner there are obtained:
(1J.b) (R)-3-[(Tetrahydro-2H-pyran-2-yl)oxy]5Z,8Z-tetradecadienal;
(1J.c) (R)-3-[(Tetrahydro-2H-pyran-2-yl)oxy]-6Z-tetradecenal.

1K. Preparation of the esters of Formulae XIII and IX (1K.a) 3.02 g of t-butyl (R)-3-hydroxy-5Z,8Z-tetradecadienoate and 2.5 ml of freshly distilled 3,4-dihydro-2H-pyran are dissolved in 300 ml of methylene chloride and cooled to 3° C. Thereafter 40 mg of p-toluenesulphonic acid monohydrate are added whereby the temperature rises to 8° C. The mixture is stirred until the reaction has finished. Thereupon, the solution is washed with a mixture of 125 ml of aqueous saturated sodium chloride solution, 125 ml of aqueous saturated sodium hydrogen carbonate and 250 ml of water. After drying the solution is filtered and the solvent is removed. There is obtained t-butyl (R)-8-[(tetrahydro-2H-pyran -2-yl)oxy]5Z,8Z-tetradecadienoate.

(1K.b) In an analogous manner there is obtained:
Methyl 2-hexyl-3-oxo-5-[(tetrahydro-2H-pyran -2-yl)-oxy]hexadecanoate, m.p. 37°–38° C.

1L. Preparation of an alcohol of Formula XI 5 g of a 55% sodium hydride dispersion are washed with hexane and treated with 600 ml of THF. A solution of 18.9 g of methyl 2-acetyloctanoate in 80 ml of THF is added dropwise while cooling. After stirring for 2 hours the mixture is cooled to −10° C. and treated while cooling with 65 ml of butyl lithium (1.6M/hexane). The reaction mixture is subsequently left at this temperature for 1 hour. A solution of 19.7 g of dodecanal in 80 ml of THF is added dropwise at −10° C. The mixture is left to warm to room temperature and stirred for a further 2 hours. The reaction mixture is hydrolyzed with 100 ml of 2N hydrochloric acid and then evaporated. The residue is extracted with ether and the ethereal phase is dried and evaporated. After chromatography on silica gel there are obtained 10.3 of methyl 2-hexyl-5-hydroxy-3-oxo-hexadecanoate, m.p. 38°-39° C.

1M. Preparation of an ester of Formula XIII-A

A solution of 0.51 g of diisopropylamine in 20 ml of THF is treated with 3.13 ml of 1.6 molar solution of butyl lithium in hexane at 0° C. The mixture is then cooled to −78° C. and 2.3 g of heptyltriphenyl phosphonium bromide are added thereto and the mixture is left at this temperature for 5 minutes. Subsequently, a solution of ethyl 5-formyl-(R)-3-[(tetrahydro-2H-pyran-2-yl)oxy]pentanecarboxylate in 10 ml of THF is added dropwise thereto. The mixture is left to stir at room temperature overnight. The reaction mixture is treated with water extracted with ether, dried and evaporated in vacuo. The residue is chromatographed over silica gel with toluene-ethyl acetate (9:1) and there is obtained 0.5 g of ethyl (R)-3-[(tetrahydro-2H-pyran-2-yl)oxy]-6Z-tetradecenecarboxylate.

1N. Preparation of an aldehide of Formula XVII

A solution of 2.56 g of methyl (R)-3-[(tetrahydro-2H-pyran-2-yl)oxy]-6-heptenoate in 40 ml of ethyl acetate is treated with ozone at −75° C. After the reaction has finished 0.1 g of Pd-on-carbon is added thereto and the mixture is hydrogenated at room temperature. After the hydrogen uptake has finished one filters off the catalyst, washes with ethyl acetate and evaporates in vacuo. There is obtained crude methyl 5-formyl-(R)-3-[(tetrahydro-2H-pyran-2-yl)oxy]-pentanecarboxylate.

1.O Preparation of the acids of Formula V into their stereoisomers (1.O.a) 15.4 g of a diastereomer mixture of 2-hexyl-3-hydroxy-(R)-5 [(tetrahydro-2H -pyran-2-yl)oxy]hexadecanoic acid are dissolved in 160 ml of ethanol and 800 mg of toluene-4-sulphonic acid monohydrate are added. The reaction mixture is heated to 55°-60° C. until the reaction has finished. The solvent is removed in vacuo and the residue is dissolved in 160 ml of dichloromethane. The solution is stirred at room temperature for 1 hour. The reaction mixture is evaporated. The material obtained is chromatographed on silica gel. There is obtained tetrahydro-3-hexyl-4-hydroxy-(R)-6-undecyl-2H-pyran-2-one, m.p. 95°-96° C.

(1.O.b) 3 g of a diastereomer mixture of tetrahydro-3-hexyl-4-hydroxy-(R)-6-undecyl-2H-pyran-2-one are dissolved in 300 ml of acetone. 3 ml of Jones' reagent are added dropwise while stirring in such a manner that the temperature does not exceed 25° C. After 3 hours the reaction mixture is poured into 700 ml of H₂O. The lactone Precipitates out and is filtered off. After recrystallization in ether/n-hexane there are obtained 1.7 g of tetrahydro-3-hexyl-4-oxo-(R)-6-undecyl-2H-pyran-2-one, m.p. 112.5°-113.5° C.

(1.O.c) 8 g of an isomer mixture of tetrahydro-3-hexyl-4-oxo-(R)-6-undecyl-2H-pyran-2-one are dissolved in 2 l of ethyl acetate and 3 g of PtO₂ are added. The mixture is then hydrogenated (50) bar for 12 hours. The catalyst is filtered off and the solution is evaporated. After recrystallization there are obtained 7 g of (3S,4S,6R)-tetrahydro-3-hexyl-4 -hydroxy-6 undecyl-2H-pyran-2-one, m.p. 108°-109° C.

(1.O.d) 1.5 g of (3S,4S,6R)-tetrahydro-3-hexyl-4-hydroxy-6-undecyl-2H-pyran-2-one are dissolved in 8 ml of DMF. 0.85 g of t-butyldimethylchlorosilane in 4 ml of DMF are then added dropwise. The mixture is stirred for 48 hours. The reaction mixture is poured into 100 ml of ether and washed with 1N hydrochloric acid. The organic phase is dried, filtered and evaporated. The material obtained is chromatographed on silica gel. There are obtained 1.26 g of (3S,4S,6R)-tetrahydro-3-hexyl 4-[(t-butyldimethylsilyl)oxy-]6-undecyl-2H-pyran-2-one, MS: 411 (M+-t-buytl), (1 O.e) 0.3 g of (3S,4S,6R)-tetrahydro-3-hexyl -4-[(t-butyldimethylsilyl)oxy]-6-undecyl-2H-pyran-2-one is dissolved in mixture of 12 ml of dioxan and 0.64 ml of 1N aqueous potassium hydroxide. The mixture is stirred overnight. The reaction mixture is then evaporated and the residue is dissolved in 10 ml of hexamethylphosphortriamide. 0.35 ml of benzyl bromide is added. The mixture is stirred for 2 days. The reaction mixture is poured into water and extracted with ether. The ether phase is dried filtered and evaporated. The oil is chromatographed on silica gel. There are obtained 330 mg of benzyl (2S,3S,5R)-2-hexyl-3 -[(t-butyldimethylsilyl)oxy[-5-hydroxyhexadecanoate, MS: 519 (M+-t-butyl).

(1.O.f) 350 mg of benzyl (2S,3S,5R)-2-hexyl-3-[(t-butyldimethylsilyl)oxy-5 -hydroxyhexadecanoate and 0.5 ml of freshly distilled 3,4-dihydro-2H-pyran are dissolved in 10 ml of methylene chloride and cooled to −15° C. A crystal of p-toluenesulphonic acid monohydrate is added thereto. The mixture is stirred until the reaction has finished. Thereupon, the solution is evaporated and the residue is chromatographed on silica gel. There are obtained 330 mg of benzyl (2S,3S,5R)-2-hexyl-3-[(t-butyldimethylsilyl)-oxy]-5-[(tetrahydro-2H-pyran-2-yl)oxy]hexadecanoate. MS: 603 (M+-t-butyl).

(1.O.g) 480 mg of benzyl (2S,3S,5R)-2-hexyl-3-[(t-butyl-dimethylsilyl)oxy]-5 -[(tetrahydro-2H-pyran-2-yl)oxy]hexadecanoate and 350 mg of tetrabutylammonium fluoride trihydrate are dissolved in 8 ml of THF and stirred for 12 hours. After evaporation the residue is dissolved in 50 ml of ether and washed with water. The ethereal phase is dried and evaporated. The crude product is chromatographed on silica gel. There are obtained 240 mg of benzyl (2S,3S,5R)-2-hexyl-3-hydroxy-5 -[(tetrahydro-2H-pyran-2-yl)oxy]hexadecanoate,, MS: 463 [(M+H)+-dihydro-2H-pyran-2-yl].

(1.O.h) 430 mg of benzyl (2S 3S,5R)-2-hexyl-3-hydroxy-5-[(tetrahydro-2H-pyran-2-yl)oxy]hexadecanoate in 10 ml of THF are treated with Pd/C 10% and hydrogenated for 3 hours. The catalyst is filtered off and, after evaporation of the filtrate, the crude product is chromatographed on silica gel. There is obtained (2S,3S,5R)-2-hexyl-3-hydroxy-5-[(tetrahydro-2H -pyran-2-yl)oxy]hexadecanoic acid.

EXAMPLE 2

2A. Manufacture of an oxetancne of Formula I 9 mg of (S)-leucine 1-[(2S,3S)-3-hexyl-4-oxo-2-oxetanyl)methyl]dodeoyl ester are dissolved in 0.3 ml of THF and 1.6 μl of formic acid/acetic acid anhydride are added thereto. The reaction has finished in a short time. 3 ml of diethyl ether are added thereto and the mixture is washed with 2% sodium hydrogen carbonate solution. The organic phase is then dried over sodium sulphate, filtered and evaporated. The residue is chromatographed on silica gel. There is obtained N-formyl-(S)-leucine (S)-1-[[(2S,3S) -3-hexyl-4-oxo-2oxetanyl]- methyl]dodecyl ester, $[\alpha]_D^{25} = -31.9°$ (c=0.345, CHCl$_3$).

2B. Preparation of an oxetanone of Formula I''

12 mg of N-[(benzyloxy)carbonyl]-L-leucine (S)-1-[[(2S,3S)-3-hexyl-4-oxo-2-oxetanyl]methyl]dodecyl ester are dissolved in 0.5 ml of THF and hydrogenated at room temperature in the presence of 5 mg of 10% Pd/C. After the reaction has finished the catalyst is filtered off and the filtrate is evaporated. The product. (S)-leucine 1-[[(2S,3S)-3-hexyl-4-oxo-2-oxetanyl)methyl]dodecyl ester, is used directly in the formulation reaction 2A.

2C. Preparation of an oxetanone of Formula I'''

45 mg of N-[(benzyloxy)carbonyl]-L-leucine are dissolved in 0.5 ml of methylene chloride with the exclusion of moisture and cooled to 2°-3° C. 17 mg of dicyclohexylcarbodiimide are added thereto and the mixture is stirred for 15 minutes. The white crystals are filtered off and the filtrate is evaporated. The residue is dissolved in 0.5 ml of N,N-dimethylformamide and this solution is added to 27 mg of (3S,4S)-3-hexyl-4-[(S)-2-hydroxy-tridecyl]-2-oxetanone and 1 mg of 4-dimethylaminopyridine in 0.5 ml of DMF. The mixture is then diluted with water and extracted with diethyl ether. The combined organic phases are dried over sodium sulphate, filtered and evaporated. After chromatography on silica gel there is obtained N-[(benzyloxy)carbonyl]-L-leucine (S)-1-[[(2S,3S)-3-hexyl-4-oxo-2-oxetanyl]methyl]dodecyl ester as white crystals of melting point 43°-46° C.

2D. Preparation of an alcohol of Formula III'

1.23 g of (3S,4S)-4-[(S)-2-(tert-butyldimethylsiloxy)-tridecyl]-3-hexyl-2-oxetanone are dissolved in 6 ml of methanol and heated to reflux with the addition of 1.05 g of DOWEX 50W-X8 (acidic cation exchanger based on polymeric divinylbenzene containing sulphonic acid residues). The ion exchanger is filtered off and the filtrate is evaporated. The residue is chromatographed on silica gel. After recrystallization from hexane there is obtained (3S,4S)-3-hexyl-4-[(S)-2-hydroxytridecyl]-2-oxetanone of melting point 63°-64° C.

2E. Preparation of an ether of Formula IV (in (S)-form)

In analogy to Example (1C.a), (3S,4S)-4-[(S)-2-(tert.-butyldimethylsiloxy)tridecyl]-3-hexyl-2-oxetanone, which contains about 20% of (cis)-4-[2-tert-butyldimethylsiloxy)tridecyl]-3 -hexyl-2-oxetanone, is obtained from a diastereomer mixture which contains predominantly (2S,3S,5S)-5 (tert-butyldimethylsiloxy)-2 -hexy-3-hydroxyhexadecanoic acid.

2F. Preparation of the acids of Formula V (in (S)-form)

430 mg of a diastereomer mixture, which consists predominantly of methyl (2S,3S,5S)-5-(t-butyldimethylsiloxy)-2-hexyl-3 -hydroxyhexadecanoate, are taken up in 8.6 ml of 2N methanolic potassium hydroxide solution and stirred until the reaction has finished. The reaction mixture is poured into water and acidified by the addition of 2N hydrochloric acid. After repeated exrraction with diethyl ether the combined extracts are dried, filtered and evaporated. The residue is chromatographed on silica gel. The thus-obtained carboxylic acid is processed directly.

2G. Preparation of an ester of Formula VI (in (S)-form)

In an analogy to Example 1F.a), a diastereomer mixture which consists predominantly of methyl (2S,3S,5S)-5-(t-butyldimethylsiloxy)-2-hexyl-3 -hydroxyhexadecanoate is obtained as a colourless oil, IR: 1719, 1361,1254, 1076, 836, 774 cm$^{-1}$, from a diastereomer mixture which consists predominantly of methyl (3S,5S)-5-(t-butyldimethyl-siloxy)-3-hydroxyhexadecanoate.

2H. Preparation of esters of Formulae VIII and XV (in (S)-form)

(2H.a) 14.5 g of a diastereomer mixture, the main component of which is (R)-2-hydroxy-1,2,2-triphenylethyl (3S,5S)-5-(t-butyldimehtylsiloxy)-3-hydroxyhexadecanoate, are suspended in 145 ml of methanol. 21.5 ml of 1N methanolic sodium methylate solution are added thereto and the mixture is stirred at room temperature for 1 hour. The solution is poured into 700 ml of saturated ammonium chloride solution. The mixture is extracted once with 200 ml of diethyl ether and then twice with 100 ml of diethyl ether. The combined extracts are dried, filtered and evaporated. The residue is taken up in 100 ml of n-hexane and stirred in an ice-bath. The white crystals are filtered off under suction and the filtrate is evaporated. The residue is chromatographed on silica gel. There is obtained a diastereomer mixture as an oil which consists predominantly of methyl (3S,5S)-5-(t-butyldimethylsiloxy)-3-hydroxyhexadecanoate. IR: 3464, 1739, 1255, 1171, 1087, 836, 775 cm$^{-1}$.

(2H.b) In an analogous manner.
methyl (S)-3-hydroxytetradecanoate which contains about 15% of the (R)-enantiomer, m.p. 36°-38° C., is obtained
from (R)-2-hydroxy-1,2,2-triphenylethyl (S)-3-hydroxytetradecanoate, which contains about 15% of the (R)-enantiomer.

2I. Preparation of ester orecursors to the esters VIII and XV (2I.a) 9.75 g of (R)-α-(hydroxydiphenylmethyl)benzyl acetate in 100 ml of THF are cooled to −76° C. under argon. A solution of 2 molar equivalents of lithium diisopropylamide is then added dropwise. The mixture is left to warm to 0° C. and is stirred for 10 minutes. The mixture is then against cooled to −76° C., 10.05 g of (S)-3-(t-butyldimethylsiloxy)tetradecanal in 20 ml of THF are added dropwise thereto and the mixture is stirred for one hour. The mixture is hydrolyzed by treatment at −76° C. to −70° C. with 25 ml of saturated ammonium chloride solution and left to warm to room temperature. The aqueous phase is separated. After washing with water the organic phase is dried, filtered and evaporated. The residue is taken up in diethyl ether and stirred. Insoluble material is removed by filtration. The solvent is removed in vacuo and the residue is recrystallized several times from acetonitrile. There is obtained a diastereomer mixture, the main component of which consists of (R)-2-hydroxy-1,2,2-triphenylethyl (3S,5S)-5-(t-butyldimethylsiloxy)-3-hydroxyhexadecanoate, m.p. 90°-92° C.

(2I.b) In an analogous manner (R)-2-hydroxy-1,2,2-triphenylethyl (S)-3-hydroxytetradecanoate, which contains about 15% of the 3(R)-isomer, of melting point 112°-115° C., is obtained from dodecanal and (R)-α-(hydroxydiphenylmethyl)benzyl acetate.

2J. Preparation of an aldehyde of Formula VII (in (S)-form)

In analogy to Example 1J.a), (S)-3-(t.butyldimethylsiloxy)tetradecanal, which contains about 15% of the (R)-enantiomer, is obtained as a colourless oil of boiling point 132°–140° C./0.6 mm from methyl (S)-3-(t-butyldimethylsiloxy)tetradecanoate which likewise contains about 15% of the (R)-enantiomer.

2K. Preparation of an ether of Formula XIII (in (S)-form)

12.9 g of methyl (S)-3-hydroxytetradecanoate are dissolved in 50 ml of DMF under argon 9.0 g of t-butyldimethylchlorosilane are added thereto, 8.5 g of imidazole are then added portionwise and the mixture is left to stir for 17 hours. The reaction mixture is poured into 300 ml of water and extracted three times with 50 ml of diethyl ether. The combined organic phases are dried, filtered and evaporated. By distillation at 140°–145° C./0.07 mm there is obtained methyl (S)-3-(t-butyldimethylsiloxy)tetradecanoate as a colourless oil.

What is claimed is:

1. A process for the preparation of compounds of the formula

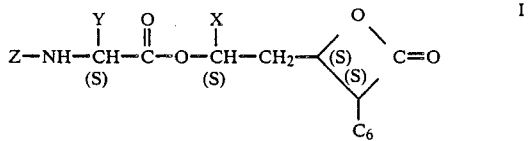

wherein X is undecyl or 2Z,5Z-undecadienyl; $C_6$ is n-hexyl; Y is isobutyl and Z is formyl
which process comprises esterifying an acid of the formula

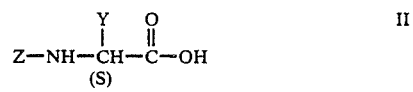

wherein Z and Y are as defined in Formula I; with an alcohol of the formula

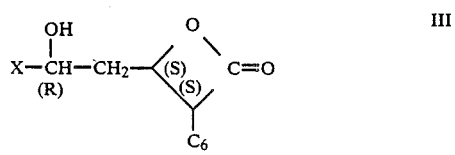

wherein X, $C_6$, Y and Z are as defined in Formula I.

2. A process according to claim 1 wherein the esterification is carried out in a solvent and in the presence of triphenylphosphine and diethyl azodicarboxylate.

3. A process according to claim 2 wherein said solvent is tetrahydrofuran.

4. A process according to claim 3 wherein the temperature is maintained at about room temperature.

5. A process according to claim 4 wherein said compound of Formula I is N-formyl-L-leucine (S)-1-[[(2S,3S)-3-hexyl-4-oxo-2-oxetanyl]methyl]dodecyl ester.

* * * * *